US006649776B2

(12) United States Patent
Manzer et al.

(10) Patent No.: US 6,649,776 B2
(45) Date of Patent: Nov. 18, 2003

(54) METHYLENELACTONE SYNTHESIS IN SUPERCRITICAL FLUIDS

(75) Inventors: Leo E. Manzer, Wilmington, DE (US); Keith W. Hutchenson, Lincoln University, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/337,542

(22) Filed: Jan. 7, 2003

(65) Prior Publication Data
US 2003/0158425 A1 Aug. 21, 2003

Related U.S. Application Data
(60) Provisional application No. 60/346,361, filed on Jan. 7, 2002.

(51) Int. Cl.[7] .............................................. C07D 307/02
(52) U.S. Cl. ........................ 549/295; 549/266; 549/273
(58) Field of Search ................................ 549/295, 273, 549/266

(56) References Cited

U.S. PATENT DOCUMENTS

| 5,166,357 A | 11/1992 | Orlek et al. |
| 6,232,474 B1 | 5/2001 | Brandenburg et al. |
| 6,313,318 B1 | 11/2001 | Coulson et al. |

FOREIGN PATENT DOCUMENTS

JP 10120672 5/1998

OTHER PUBLICATIONS

A. W. Murray and R. G. Reid, Convenlent Synthesis of a–Epoxylactones (4–Oxo–1,5–dioxaspiro[2.4]heptanes and –[2.5]pctanes), Synthesis, 1985, vol. 1, pp. 35–38.
Keith Hutchenson, Organic Chemical Reactions and Catalysis in Supercritical Fluid Media, Supercritical Fluid Technology in Materials Science and Engineering, Y. P/ Sun (ed), Marcel Dekker: New York (2002) pp. 87–187.

*Primary Examiner*—Amelia Owens
(74) *Attorney, Agent, or Firm*—Inna Y. Belopolsky

(57) ABSTRACT

Alpha-methylenelactones are produced from butyrolactone and valerolactone by the addition of formaldehyde in a supercritical fluid in the presence of a catalyst and a phase transfer agent.

28 Claims, No Drawings

METHYLENELACTONE SYNTHESIS IN SUPERCRITICAL FLUIDS

FIELD OF INVENTION

The invention pertains to a method to produce α-methylenelactones from lactones by the addition of formaldehyde in a supercritical fluid in the presence of a catalyst and a phase transfer agent.

BACKGROUND

Alpha-methylenelactones have been the subject of intensive synthetic studies. Specifically, the α-methylene-γ-butyrolactone group is an important structural feature of many sesquiterpenes of biological importance. In addition, α-methylene-γ-butyrolactones are regarded as potential key monomers in both homopolymers and copolymers. Some of the current synthetic routes suffer from low yields, byproduct formation and expensive starting materials. The need exists for high conversion/high yield synthetic routes that can be used commercially.

Essentially all approaches to synthesize α-methylene-γ-butyrolactone are liquid-phase processes. Vapor-phase processes are described in JP 10120672 and U.S. Pat. No. 6,313,318 B1. Liquid phase processes include Murray et al. (Synthesis 1:35–38, 1985), U.S. Pat. No. 5, 166,357, and U.S. Pat. No. 6,232,474 B1. There have been no reports of using supercritical fluids (SCF) in the synthesis of methylenelactones from lactones.

The present method represents an advance in the art by offering a process that exploits several advantages of using a SCF as the reaction solvent. SCFs are attractive media for conducting chemical transformations, primarily because the solvent and transport properties of a single solution can be varied appreciably and continuously with relatively minor changes in temperature or pressure. The density variation in a SCF also influences the chemical potential of solutes and thus reaction rates and equilibrium constants. Thus, the solvent environment can be optimized for a specific reaction application by tuning the various density-dependent fluid properties. For a discussion of advantages and applications of supercritical fluid media for chemistry and catalysis, see Hutchenson, K. W., "Organic Chemical Reactions and Catalysis in Supercritical Fluid Media, " in *Supercritical Fluid Technology in Materials Science and Engineering*, Y. -P. Sun (ed.), Marcel Dekker: New York (2002), pp. 87–187.

A fluid is in the supercritical fluid state when the system temperature and pressure exceed the corresponding critical point values defined by the critical temperature ($T_c$) and pressure ($P_c$) Most useful applications of SCFs which take advantage of the unusual physical properties in this region occur in the range of reduced properties of $T_R$ (=$T/T_c$) ≈1.0–1.1 and $P_R$ (=$P/P_c$)≈1–2. However, many of the potential benefits afforded by a SCF solvent can be realized at conditions slightly subcritical in temperature or pressure.

One of the primary advantages of SCF reaction media is that the density can be varied continuously from liquid-like to gas-like values by either varying the temperature or pressure, and to a first approximation, the solvent strength of the SCF media can be related to this continuously-variable solution density. The various density-dependent physical properties (e. g., solvent polarity) also exhibit similar continuous variation in this region. In general, a SCF in the vicinity of its critical point has a liquid-like density and solvent strength, but exhibits transport properties (mass, momentum, and thermal diffusivities) that are intermediate to those of gases and liquids.

Since gaseous reactants are completely miscible with SCFs, their concentrations in SCF reaction media are significantly higher than are obtainable in conventional liquid solvents, even at appreciable pressures. These higher reactant concentrations in SCF media combined with increased component diffusivities and relatively low system viscosities can result in mass transfer rates that are appreciably higher than in liquid solvents. This can potentially shift a chemical reaction rate from mass transfer control to kinetic control in the reactor. The solubility of gaseous reactants in liquid solvents can also be enhanced by a volume expansion of the solvent with a dense supercritical fluid, which likewise results in increased mass transfer rates. Improved mass transport can also result in enhanced removal of residual solvents.

In addition to typical factors such as chemical inertness, cost, toxicity, etc., the critical temperature must be considered when selecting a potential solvent for conducting chemical transformations in the SCF regime. For practical applications, thermal and catalytic chemical reactions can only be conducted in a relatively narrow temperature range. Lower temperatures result in unacceptable reaction rates, and higher temperatures can result in significant selectivity and yield losses as well as catalyst deactivation. To obtain practical solvent densities and the corresponding density-dependent properties, this temperature optimization must be balanced against a general desire to operate in the vicinity of the mixture critical point of the reaction system to fully exploit the potential advantages afforded by SCF operation. The phase behavior of the reaction mixture, which is strongly influenced by the solvent critical temperature, is fundamentally important in defining this operating window, so one must select a solvent to provide the desired phase behavior. The phase behavior of SCF systems can also be manipulated to control the number and composition of coexisting phases, thus controlling both reaction effects as well as the separation of products or homogeneous catalysts from the reaction mixture. Finally, the addition of cosolvents can be effectively utilized to exploit specific solute interactions such as enhancing solute solubilities and influencing reaction selectivities, and equilibria.

A reason often cited for using SCF-mediated reaction processes is the potential for utilizing a reaction medium that exhibits improved safety, health, and environmental impact relative to typical organic solvents. Carbon dioxide, in particular, is generally considered environmentally benign, nontoxic, nonflammable, and inexpensive, and it is suitable for use as a SCF solvent at relatively moderate temperatures. However, there are a variety of other practical SCF solvents that potentially have better solubility characteristics than $CO_2$ as well as beneficial impact relative to conventional liquid organic solvents.

SUMMARY OF THE INVENTION

The invention is directed towards a process for preparing α-methylenelactones of Formula II comprising heating lactones of Formula I and formaldehyde in a supercritical fluid in the presence of a catalyst and a phase transfer agent:

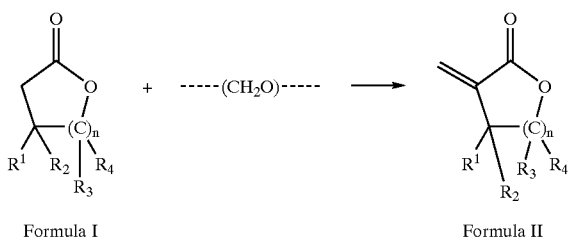

Formula I

Formula II wherein n=1–11; $R^1$, $R^2$, $R^3$ and $R^4$ taken independently are selected from the group consisting of hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom unsubstituted or substituted aromatic ring, and unsubstituted or substituted aromatic ring containing at least one heteroatom; and any two of $R^1$, $R^2$, $R^3$ and $R^4$ together can optionally form a ring. Preferably $R^1$, $R^2$, and $R^3$ are hydrogen and n is 1. More preferably the lactone of Formula I is γ-valerolactone and the α-methylenelactone of Formula II is α-methylene-γ-valerolactone, and the lactone of Formula I is γ-butyrolactone and the α-methylenelactone of Formula II is α-methylene-γ-butyrolactone.

The supercritical solvent is preferably carbon dioxide or a C1–C6 alkane, optionally substituted with Cl, F or Br; more preferably carbon dioxide, trifluoromethane, pentane or propane.

DETAILED DESCRIPTION OF THE INVENTION

In the context of this disclosure, a number of terms and abbreviations shall be utilized. The following definitions are provided.

"α-methylene-γ-butyrolactone" is abbreviated MBL

"γ-butyrolactone" is abbreviated GBL

"γ-valerolactone" is abbreviated GVL

"α-methylene-γ-valerolactone" is abbreviated MVL gamma-valerolactone alpha-methylene-gamma-valerolaction.

"Gas chromatography" is abbreviated GC.

"Nuclear magnetic resonance" is abbreviated NMR.

"Molecular weight" is abbreviated MW.

"Mass spectroscopy" is abbreviated MS.

"Supercritical fluid" is abbreviated SCF.

By "alkyl" herein is meant a straight chain or branched alkyl group, such as, methyl, ethyl, n-propyl, i-propyl, or the different butyl, pentyl and hexyl isomers. Also included are all isomers up to and including octadecyl.

By "alkenyl" herein is meant an unsaturated straight chain or branched alkyl.

By "hydrocarbyl" herein is meant a univalent group containing only carbon and hydrogen. If not otherwise stated, it is preferred that hydrocarbyl groups herein contain 1 to about 30 carbon atoms.

By "substituted" herein is meant a group that contains one or more substituent groups that are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

The present invention pertains to a process for preparing α-methylenelactones of Formula II comprising heating lactones of Formula I and formaldehyde in a supercritical fluid in the presence of a catalyst and a phase transfer agent:

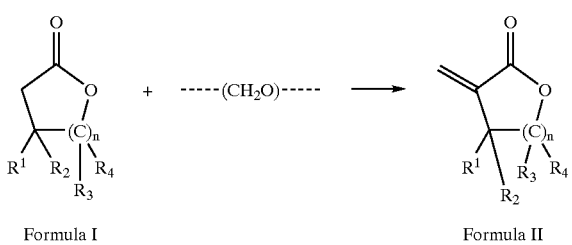

Formula I

Formula II where n=1–11; $R^1$, $R^2$, $R^3$ and $R^4$ taken independently are selected from the group consisting of hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom unsubstituted or substituted aromatic ring, and unsubstituted or substituted aromatic ring containing at least one heteroatom; and any two of $R^1$, $R^2$, $R^3$ and $R^4$ together can optionally form a ring. Preferably $R^1$, $R^2$, and $R^3$ are hydrogen. More preferably, the lactone of Formula I is γ-valerolactone and the α-methylenelactone of Formula II is (α-methylene-γ-valerolactone, and the lactone of Formula I is γ-butyrolactone and the (α-methylenelactone of Formula II is (α-methylene-γ-butyrolactone.

By "supercritical fluid" (SCF) herein is meant a state of matter for a substance or a mixture of substances that exists above the critical temperature and critical pressure of the substance or mixture. For pure substances, the critical temperature and pressure are the highest at which vapor and liquid phases can coexist. Above the critical temperature, a liquid does not form for a pure substance, regardless of the applied pressure. Similarly, the critical pressure and critical molar volume are defined at this critical temperature corresponding to the state at which the vapor and liquid phases merge. Similarly, although more complex for multicomponent mixtures, the mixture critical state is identified as the condition at which the properties of coexisting vapor and liquid phases become indistinguishable. In practice, a number of desirable properties characteristic of the SCF state are realized in the expanded liquid region that exists at temperatures and pressures slightly below this critical point. Hence, for the purposes of this document, the term "supercritical fluid" also includes such "near-critical fluids," as defined below. For a discussion of supercritical fluids, see Kirk-Othmer Encycl. of Chem. Technology, 4th Ed., Vol 23, pg.452–477.

Importantly, the subject substance will begin to manifest many of the physical traits of a supercritical fluid before conditions actually cause the change of state of matter. This phenomenon is analogous to other changes in states of matter, such as when water is heated to the boiling point. Just prior to the water reaching the temperature at which it boils, it behaves similarly to the steam it will become in terms of molecular kinetics, energy, and, of course, temperature. Just prior to a liquid or gas becoming a supercritical fluid, it also begins to manifest some of the physical properties and attributes, such as density, viscosity, diffusivity and solubility, of the supercritical fluid it will become. The mixture is termed a "near-critical fluid" when the fluid is either at or below the critical temperature and the properties begin to approach those of a supercritical fluid. For the purposes of this document, "near-critical fluid" includes those conditions where the fluid is at temperatures from about 75% of the critical temperature to about 100% of the critical temperature, and pressures from about 25% of the critical pressure to about 100% of the critical pressure.

Supercritical fluids exhibit properties intermediate between those of gases and liquids. A key feature of a SCF is that the fluid density can be varied continuously from liquid-like to gas-like densities by varying either the temperture or pressure, or a combination thereof. Various density-dependent physical properties likewise exhibit similar continuous variation in this region. Some of these properties include, but are not limited to, solvent strength (as evidenced by the solubilities of various substances in the SCF media), polarity, viscosity, diffusivity, heat capacity, thermal conductivity, isothermal compressibility, expandability, contractibility, fluidity, and molecular packing. The density variation in a SCF also influences the chemical potential of solutes and hence, reaction rates and equilibrium constants. Thus, the solvent environment in a SCF media can be optimized for a specific reaction application by tuning the various density-dependent fluid properties.

Any suitable SCF may be used in the processes of the invention, including, but not limited to, carbon dioxide, nitrous oxide, sulfur hexafluoride, fluoromethane trifluoromethane, tetrafluromethane, ethane, ethylene, propane, propanol, isopropanol, propylene, butane, butanol, isobutane, isobutene, pentane, hexane, cyclohexane, benzene, toluene, o-xylene, water, and mixtures thereof, provided that it is inert to all reagents and products. Preferred is where the supercritical fluid is carbon dioxide or a C1–C6 alkane, optionally substituted with Cl, F or Br. More preferred is where the supercritical fluid is carbon dioxide, trifluoromethane, pentane or propane.

One component of the invention is formaldehyde. Formaldehyde may be supplied in a variety of forms including as a solution (formalin) or in the form of an oligomer, cyclic oligomer, formaldehyde acetal, formaldehyde hemiacetal, or formaldehyde polymer. By formaldehyde acetal and formaldehyde hemiacetal, it is meant an acetal or hemiacetal formed from the reaction of a formaldehyde with an alcohol, such as but not limited to the reaction of paraformaldehyde with ethanol. Polymers of formaldehyde are more generally denominated polyacetals and include or are characterized by a linear polymer chain containing recurring —($CH_2O$)— units or groups. A suitable polymer of formaldehyde in the composition of the invention is polyoxymethylene, which has not been stabilized against thermal degradation as, for example, by end-capping the ends of the linear polymer chain with stabilizing end-groups. Thus, a preferred polymer of formaldehyde is paraformaldehyde, which is a lower molecular weight linear polymer available commercially as a fine powder. Another suitable polymer of formaldehyde is, for example, trioxane, a trimer of formaldehyde. Polymers of formaldehyde are described generally in U.S. Pat. No. 2,768,994. Another variety of polymers are sold under the registered trademark Delrin® by E. I. du Pont de Nemours and Company, Inc. Preferably the formaldehyde used in the instant invention is in the form of trioxane, formaldehyde hemiacetal or paraformaldehyde. The formaldehyde may also be prepared from a precursor or another form of formaldehyde in situ or immediately before contact with the other reagents.

The catalyst of the instant invention can optionally be a basic catalyst. A suitable basic catalyst can be defined either as a substance which has the ability to accept protons as defined by Bronsted, or as a substance which has an unshared electron pair with which it can form a covalent bond with an atom, molecule or ion as defined by Lewis. A further definition of basic catalysts and how to determine if a particular catalyst is basic is explained in Tanabe, K., Catalysis : Science and Technology, Vol. 2, pg. 232–273, ed. Anderson, J. and Boudart, M., Springer-Verlag, N.Y., 1981.

The basic catalysts of the invention are selected from elements from the Group I, Group II and lanthanide groups of the Periodic Table of Elements. Preferably the basic catalyst is potassium, rubidium, cesium, calcium or barium, or mixtures thereof. The catalyst may be in the form of a salt such as carbonates, hydrogen carbonates, oxides, hydroxides, acetates, and phosphates, and mixtures thereof. They may be used as powders, granules, or other particulate forms, or may be supported on an essentially inert support as is common in the art of catalysis. The catalysts may be commercially available and can prepared by any method known in the art. When supported, one preferred method involves impregnating the catalyst support by incipient wetness with one or more precursors, typically metal salts, followed by calcination.

Representative precursors include but are not limited to carbonates, hydrogen carbonates, oxides, hydroxides, acetates, and phosphates of potassium, cesium, calcium, barium, sodium, lanthanum, magnesium, cadmium, rubidium, lithium, and strontium; and mixtures thereof. The preferred precursors are potassium carbonate, lithium hydroxide, barium acetate, potassium hydroxide, sodium hydroxide, rubidium acetate, potassium phosphate, cesium acetate, calcium acetate and potassium acetate.

The catalysts of the present invention may further comprise catalyst additives and promoters that will enhance the efficiency of the catalyst. Use of these materials are common and well known in the art (see for example, Kirk-Othmer Encyclopedia of Chemical Technology, Howe-Grant Ed., Vol. 5, pp 326–346, (1993), John Wiley & Sons, New York and Ullmann's Encyclopedia of Industrial Chemistry, Vol. A5, Gerhartz et al., Eds., pp. 337–346, (1986), VCH Publishers, New York, both hereby incorporated by reference.) Particularly useful in the present invention are promoters which include, but are not limited to Au, Na, K, Cs, Ba, Re, Fe, and Cr. The relative percentages of the catalyst promoter may vary. Useful amounts of promoter will be from about 0.01% to about 50% by weight of catalyst.

The catalysts of the present invention may be supported or unsupported. Where a support is desired, suitable supports include but are not limited to silica, titania, zirconia, alumina, carbon, various zeolites and mixtures thereof. Commonly used techniques for treatment of supports with metal catalysts can be found in B. C. Gates, Heterogeneous Catalysis, Vol. 2, pp. 1–29, Ed. B. L. Shapiro, Texas A & M University Press, College Station, Tex., 1984.

Although a wide variety of phase transfer agents are known and used in the chemical industry, certain phase transfer agents work more effectively than others for a particular chemical reaction and for individual reactants. A preferred phase transfer agent is tetraheptylammonium bromide or 18-crown-6 ether. Other catalysts useful herein include but are not limited to quaternary ammonium salts, quaternary phosphonium salts, crown ethers, and polyethers. For polyethers, the phase transfer agent is a member selected from the group consisting of polyethylene glycols (PEG's) of various molecular weights (MW). PEG's with an average molecular weight from 200 to>20,000 are available commercially. The number of repeat units, n, in the PEG is an important factor in its effectiveness as a phase transfer agent. Values of n greater than or equal to 8 are generally preferred as phase transfer agents. The phase transfer agent is used in an amount of 0 to 25 weight percent, preferably 0.1 to 10 weight percent, of the reactive substrate. Phase transfer agents are common and well known in the art, see for example, Cook et al., Chim. Oggi 16(1/2):44–48 (1998); "Phase Transfer Catalysis: Fundamentals, Applications, and Industrial Perspectives" by C. M. Starks, C. L. Liotta, and M. Halpern., Chapman & Hall, Inc. 1994.

The temperature of the reaction can range from about 70° C. to about 400° C., with a preferred range of about 100° C. to about 350° C. A more preferred range is about 125° C. to about 350° C. Pressure ranges are those required to achieve supercritical or near-critical state under the reaction conditions present. The pressure of the reaction can range from about 5 to about 60 MPa, with a preferred range of about 15 to about 40 MPa. Contact time can be selected to achieve the desired yields and selectivities, which can also be enhanced by additional contact with the catalyst.

Reactors suitable for processes of the instant invention include continuous stirred tank reactor (CSTR), batch stirred tank reactor (stirred batch reactor), semi-batch stirred tank reactor, tubular reactor, fluidized bed reactor, fixed bed reactor, and trickle bed reactor. The process can be run in either batch or continuous mode as described in H. Scott Fogler, *Elements of Chemical Reaction Engineering*, 2nd Edition, Prentice-Hall Inc, CA, 1992. The process can also be run in either a single homogeneous phase over the solid catalyst, or the reactants and SCF may be in two different phases over the solid catalyst.

Separation and/or purification of the product may be performed by any process known in the art. One particularly suitable method is density reduction via pressure or temperature drop.

EXAMPLES

All reactions, except where specified, were performed according to the conditions set in Table 1 below. The reactions were conducted in a custom Hastelloy C stirred batch reactor, nominally 20 mL in volume (0.75"id×2.75" long), and equipped with two sapphire windows to allow visual observation of the phase behavior during the reaction. All reactants were in a single fluid phase. The reactor included a Teflon®-coated stir bar (E. I. du Pont de Nemours and Company, Wilmington, Del.) which was driven by an external magnetic stir plate.

The pressures shown are gauge pressures. "Conversion" indicates the percent conversion of the lactones to the methylenelactones and derivatives, and was determined by GC or GC/MS. In examples 1–4 the lactone was GBL and the methylenelactone product was MBL; in examples 5–8 the lactone was GVL and the methylenelactone product was MVL. BA catalyst is Englehardt 6729–46–01, 24% barium acetate on KA-160 silica. In the results, THAB is tetraheptylammonium bromide and 18Crwn6 is 18-Crown-6 ether. The results are shown below in Table 1.

TABLE 1

| Ex. | GBL (g) | Formaldehyde Source | (g) | Catalyst | (g) | Phase Transfer Agent | (g) | Solvent | Rxn. Temp. (° C.) | Rxn. Press. (MPa) | Rxn Time (h) | Conversion (%) |
|---|---|---|---|---|---|---|---|---|---|---|---|---|
| 1 | 0.9129 | Paraformaldehyde | 0.7021 | $K_2CO_3$ | 1.2008 | THAB | 0.2864 | $CO_2$ | 200 | 37.3 | 2 | 86.3 |
| Comp. | 0.9847 | Paraformaldehyde | 0.7013 | $K_2CO_3$ | 1.1996 | — | — | $CO_2$ | 200 | 32.6 | 2 | 65.7 |
| 2 | 0.9975 | Paraformaldehyde | 0.7066 | $K_2CO_3$ | 1.2008 | THAB | 0.2850 | $CO_2$ | 130 | 33.4 | 2 | 50.5 |
| Comp. | 0.9658 | Paraformaldehyde | 0.7005 | $K_2CO_3$ | 1.1984 | — | — | $CO_2$ | 130 | 32.3 | 2 | 22.2 |
| 3 | 0.9464 | Paraformaldehyde | 0.6998 | $K_2CO_3$ | 1.1974 | THAB | 0.1482 | $CO_2$ | 200 | 32.9 | 2 | 99.3 |
| 4 | 1.0254 | Paraformaldehyde | 0.7008 | $K_2CO_3$ | 2.4009 | THAB | 0.2854 | $CHF_3$ | 200 | 36.3 | 4 | 40.6 |

| Ex. | VBL (g) | Formaldehyde Source | (g) | Catalyst | (g) | Phase Transfer Agent | (g) | Solvent | Rxn. Temp. (° C.) | Rxn. Press. (MPa) | Rxn Time (h) | Conversion (%) |
|---|---|---|---|---|---|---|---|---|---|---|---|---|
| 5 | 1.1815 | Paraformaldehyde | 0.7024 | $K_2CO_3$ | 2.0088 | THAB | 0.1484 | $CO_2$ | 201 | 32.3 | 4 | 68.5 |
| 6 | 1.1684 | Paraformaldehyde | 0.7013 | $K_2CO_3$ | 2.0106 | THAB | 0.3026 | $CO_2$ | 200 | 32.9 | 4 | 69.9 |
| 7 | 1.1907 | Paraformaldehyde | 0.7022 | $K_2CO_3$ | 2.0050 | THAB | 0.4645 | $CO_2$ | 199 | 33.8 | 4 | 89.8 |
| 8 | 1.0683 | Paraformaldehyde | 0.7014 | $K_2CO_3$ | 2.0104 | 18Crwn6 | 0.1621 | $CO_2$ | 200 | 33.5 | 4 | 81.6 |
| Comp. | 1.2134 | Paraformaldehyde | 0.7014 | $K_2CO_3$ | 2.0836 | — | — | $CO_2$ | 200 | 33.5 | 4 | 46.5 |

Example 9

The following comparative experiments were conducted in a continuous fixed bed reactor consisting of a 0.375-inch o.d.×0.065-inch wall×11-inch long 316 stainless steel tube packed with powder catalyst. The reactor was heated by electrical band heaters mounted around an aluminum block enclosing the reactor. Process lines were heated by electrical heating tape. The lactone was combined with the formaldehyde precursor (e. g., ethanol hemiacetal) as a liquid feed and metered to the reactor with a syringe pump. $CO_2$ was used as the SCF solvent phase, and the $CO_2$ flow rate was metered with a second syringe pump. The two streams were heated and combined in a static mixer prior to entering the reactor. Liquid-phase reactor effluent samples were collected downstream in an ice bath after venting the carbon dioxide, and reaction products were quantified by gas chromatography. The reactor pressure was controlled by either a control valve or backpressure regulator located downstream of the reactor.

The reactor was charged with 9.1 g of potassium carbonate catalyst. The reactant feed solution consisted of 7.8 mol % γ-valerolactone and 0.4% of the phase transfer agent 18-crown-6 ether with the balance made up with an ethanol hemiacetal solution as the formaldehyde precursor. The ethanol hemiacetal was prepared by refluxing a 25 wt % paraformaldehyde solution in ethanol for four hours at 95° C. followed by cooling to room temperature and filtration. This solution resulted in a 4:1 ratio of formaldehyde to γ-valerolactone in the reactor feed, which was metered at a rate resulting in a weight hour space velocity in the reactor of 0.13 g γ-valerolactone/(g catalyst-h). The $CO_2$ flow rate was metered independently to give a final reactant concentration of 5 mol % in the reactor feed. Following this run, the reactor was loaded with 9.1 g of fresh potassium carbonate catalyst, and the experiment was repeated with a reactant feed solution consisting of 7.8 mol % γ-valerolactone with the balance made up with the same ethanol hemiacetal solution as the formaldehyde precursor (i.e., no added phase transfer agent). The reactor was operated at a temperature of 252° C. and a pressure of about 35 MPa for both experiments. The corresponding reaction profile showed significantly higher conversion of the γ-valerolactone reactant to the methylene lactone product, as summarized below:

| Run Time (h) | γ-VL Conversion w/ 18-Crown-6 Ether (%) | γ-VL Conversion w/o 18-Crown-6 Ether (%) |
| --- | --- | --- |
| 0.67 | 41.5 | — |
| 0.84 | — | 32.9 |
| 1.09 | — | 34.2 |
| 1.19 | 45.4 | — |
| 1.86 | 52.1 | — |
| 1.93 | — | 33.3 |
| 2.46 | 60.9 | 38.6 |
| 2.83 | 64.7 | — |
| 3.00 | — | 40.2 |
| 3.09 | 69.5 | — |
| 3.89 | 78.6 | — |

What is claimed is:

1. A process for preparing α-methylenelactones of Formula II, the method comprising heating lactones of Formula I and formaldehyde in a supercritical fluid in the presence of a catalyst and a phase transfer agent:

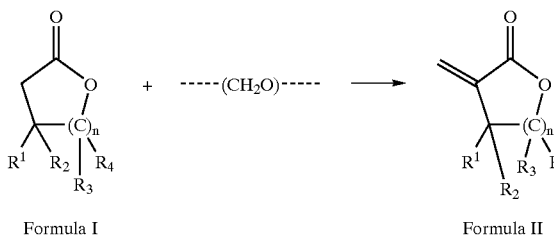

Formula I                    Formula II wherein, n=1–11;

$R^1$, $R^2$, $R^3$ and $R^4$ taken independently are selected from the group consisting of hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom unsubstituted or substituted aromatic ring, and unsubstituted or substituted aromatic ring containing at least one heteroatom; and any two of $R^1$, $R^2$, $R^3$ and $R^4$ together can optionally form a ring.

2. The process of claim 1 wherein $R^1$, $R^2$, and $R^3$ are hydrogen and n is 1.

3. The process of claim 1 wherein the lactone of Formula I is γ-valerolactone and the α-methylenelactone of Formula II is α-methylene-γ-valerolactone.

4. The process of claim 1 wherein the lactone of Formula I is γ-butyrolactone and the α-methylenelactone of Formula II is α-methylene-γ-butyrolactone.

5. The process of claim 1 wherein the supercritical fluid is carbon dioxide or a C1–C6 alkane, optionally substituted with Cl, F or Br.

6. The process of claim 5 wherein the supercritical fluid is carbon dioxide, pentane, trifluoromethane or propane.

7. The process of claim 1 wherein the catalyst is a basic catalyst.

8. The process of claim 7 wherein the basic catalyst comprises an element selected from the group consisting of Group I, Group II, Lanthanide Group, and mixtures thereof.

9. The process of claim 8 wherein the basic catalyst comprises potassium, rubidium, cesium, calcium and barium, and mixtures thereof.

10. The process according to claim 9 wherein the basic catalyst is prepared from a precursor selected from the group consisting of Group I, Group II, and Lanthanide Group oxides, hydroxides, carbonates, hydrogen carbonates, silicates, oxalates, carboxylates, acetates and phosphates, and mixtures thereof.

11. The process according to claim 10 wherein the precursor is selected from the group consisting of carbonates, hydrogen carbonates, oxides, hydroxides, acetates, and phosphates of potassium, cesium, calcium, barium, sodium, lanthanum, magnesium, cadmium, rubidium, lithium, and strontium; and mixtures thereof.

12. The process according to claim 11 wherein the precursor is selected from the group consisting of potassium carbonate, lithium hydroxide, barium acetate, potassium hydroxide, sodium hydroxide, rubidium acetate, cesium acetate, calcium acetate, potassium acetate and potassium phosphate.

13. The process according to claim 7 wherein the basic catalyst is potassium carbonate.

14. The process according to claim 1 wherein the catalyst is optionally supported on a suitable support.

15. The process according to claim 1 wherein the catalyst optionally comprises a catalyst promoter.

16. The process according to claim 15 wherein the catalyst promoter is selected from the group consisting of Au, Na, K, Cs, Ba, Re, Fe, W and Cr.

17. The process according to claim 14 wherein the suitable support is selected from the group consisting of silica, titania, zirconia, alumina, carbon, zeolites and mixtures thereof.

18. The process according to claim 14 wherein the suitable support is silica.

19. The process according to claim 18 wherein the catalyst is selected from the group consisting of barium, potassium, rubidium, cesium, and calcium, and mixtures thereof.

20. The process according to claim 1 wherein the formaldehyde is selected from the group consisting of trioxane, anhydrous formaldehyde, formalin, formaldehyde oligomer, formaldehyde cyclic oligomer, formaldehyde acetal, formaldehyde hemiacetal, and formaldehyde polymer.

21. The process according to claim 20 wherein the formaldehyde is in the form of formalin, trioxane, formaldehyde hemiacetal or paraformaldehyde.

22. The process according to claim 1 wherein the lactones of Formula I, the formaldehyde, and the supercritical fluid are in a homogeneous phase.

23. The process according to claim 1 wherein the lactones of Formula I and the formaldehyde are in a homogeneous phase and the supercritical fluid is in a second phase.

24. The process according to claim 1 wherein the temperature of the process is about 70° C. to about 400° C., and the pressure is that which is required to achieve supercritical or near-critical state under the reaction conditions.

25. The process according to claim 24 wherein the temperature is about 100° C. to about 350° C., and the pressure is about 5 to about 60 MPa.

26. The process according to claim 24 wherein the temperature is about 125° C. to about 350° C., and the pressure is about 15 to about 40 MPa.

27. The process according to claim 1 wherein the phase transfer agent is selected from the group consisting of quaternary ammonium salts, quaternary phosphonium salts, crown ethers, and polyethers.

28. The process according to claim 27 wherein the phase transfer agent is tetraheptylammonium bromide or 18-crown-6 ether.

* * * * *